(12) United States Patent
Ferrand et al.

(10) Patent No.: US 11,927,707 B2
(45) Date of Patent: *Mar. 12, 2024

(54) DENSE HIGH-SPEED SCINTILLATOR MATERIAL OF LOW AFTERGLOW

(71) Applicant: LUXIUM SOLUTIONS, LLC, Hiram, OH (US)

(72) Inventors: Bernard Ferrand, Voreppe (FR); Bruno Viana, Montgeron (FR); Ludivine Pidol, Cachan (FR); Pieter Dorenbos, GM Rijswijk (NL)

(73) Assignee: LUXIUM SOLUTIONS, LLC, Hiram, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/991,989

(22) Filed: Nov. 22, 2022

(65) Prior Publication Data
US 2023/0077952 A1 Mar. 16, 2023

Related U.S. Application Data

(60) Continuation of application No. 17/114,824, filed on Dec. 8, 2020, now abandoned, which is a continuation
(Continued)

(30) Foreign Application Priority Data

Aug. 9, 2004 (FR) .................................... 0451815

(51) Int. Cl.
*G01T 1/20* (2006.01)
*C09K 11/74* (2006.01)
(Continued)

(52) U.S. Cl.
CPC .......... *G01T 1/2023* (2013.01); *C09K 11/745* (2013.01); *C09K 11/77742* (2021.01);
(Continued)

(58) Field of Classification Search
CPC ................ G01T 1/2023; C09K 11/745; C09K 11/77742; C09K 11/77744; G21K 4/00; A61B 6/4258
See application file for complete search history.

(56) References Cited

U.S. PATENT DOCUMENTS 4,747,973 A   5/1988   Cusano et al.
4,783,596 A   11/1988  Riedner et al.
(Continued)

FOREIGN PATENT DOCUMENTS

CN   1926218 A    3/2007
CN   102477580 A  5/2012
(Continued)

OTHER PUBLICATIONS

Maria D. Alba et al, "Formation of High-Temperature Lutetium Disilicate from Lutetium-Saturated Aluminosilicates in Mild Conditions. Incorporation of Si and Al XAS Techniques to the Study of These Systems", J. Phys. Chem., 100, 1996, pp. 19559-19567.
(Continued)

*Primary Examiner* — Marcus H Taningco
(74) *Attorney, Agent, or Firm* — ABEL SCHILLINGER, LLP; John M. Frank

(57) ABSTRACT

The invention relates to an inorganic scintillator material of formula $Lu_{(2-y)}Y_{(y-z-x)}Ce_xM_zSi_{(1-v)}M'_vO_5$, in which:
M represents a divalent alkaline earth metal and M' represents a trivalent metal,
(z+v) being greater than or equal to 0.0001 and less than or equal to 0.2;
z being greater than or equal to 0 and less than or equal to 0.2;
v being greater than or equal to 0 and less than or equal to 0.2;
x being greater than or equal to 0.0001 and less than 0.1; and
y ranging from (x+z) to 1.
(Continued)

In particular, this material may equip scintillation detectors for applications in industry, for the medical field (scanners) and/or for detection in oil drilling. The presence of Ca in the crystal reduces the afterglow, while stopping power for high-energy radiation remains high.

19 Claims, 3 Drawing Sheets

Related U.S. Application Data of application No. 16/400,195, filed on May 1, 2019, now Pat. No. 10,890,670, which is a continuation of application No. 15/358,341, filed on Nov. 22, 2016, now Pat. No. 10,324,198, which is a continuation of application No. 14/039,888, filed on Sep. 27, 2013, now Pat. No. 9,534,170, which is a continuation of application No. 13/214,648, filed on Aug. 22, 2011, now Pat. No. 8,574,458, which is a division of application No. 12/622,881, filed on Nov. 20, 2009, now Pat. No. 8,034,258, which is a division of application No. 11/573,323, filed as application No. PCT/FR2005/050658 on Aug. 8, 2005, now Pat. No. 7,651,632.

(51) Int. Cl.
  *C09K 11/77* (2006.01)
  *G01T 1/202* (2006.01)
  *G21K 4/00* (2006.01)
(52) U.S. Cl.
  CPC .......... *C09K 11/77744* (2021.01); *G21K 4/00* (2013.01); *A61B 6/4258* (2013.01)

(56) References Cited

U.S. PATENT DOCUMENTS

| | | | |
|---|---|---|---|
| 5,003,181 A | 3/1991 | Morlotti | |
| 5,998,925 A | 12/1999 | Shimizu et al. | |
| 6,093,347 A | 7/2000 | Lynch et al. | |
| 6,278,832 B1 | 8/2001 | Zagumennyi | |
| 6,323,489 B1 | 11/2001 | McClellan | |
| 6,437,336 B1 | 8/2002 | Pauwels et al. | |
| 6,498,828 B2 | 12/2002 | Jiang | |
| 6,624,420 B1 | 9/2003 | Chai et al. | |
| 6,921,901 B1 | 7/2005 | Chai et al. | |
| 7,102,135 B2 | 9/2006 | Lecoq | |
| 7,132,060 B2 | 11/2006 | Zagumennyi | |
| 7,138,074 B1 | 11/2006 | Nakamura | |
| 7,151,261 B2 | 12/2006 | Chai | |
| 7,166,845 B1 | 1/2007 | Chai | |
| 7,180,068 B1 | 2/2007 | Brecher et al. | |
| 7,531,036 B2 | 5/2009 | Shimura et al. | |
| 7,618,491 B2 | 11/2009 | Kurata et al. | |
| 7,651,632 B2 | 1/2010 | Ferrand et al. | |
| 7,692,153 B2 | 4/2010 | Shimizu et al. | |
| 7,749,323 B2 | 7/2010 | Shimura et al. | |
| 8,034,258 B2 | 10/2011 | Ferrand et al. | |
| 8,062,419 B1 | 11/2011 | Andreaco et al. | |
| 8,158,948 B2 | 4/2012 | Chou | |
| 8,278,624 B2 | 10/2012 | Koschan et al. | |
| 8,394,195 B2 | 3/2013 | Andreaco et al. | |
| 8,574,458 B2 | 11/2013 | Ferrand et al. | |
| 8,617,422 B2 | 12/2013 | Koschan et al. | |
| 8,999,281 B2 | 4/2015 | Kurata et al. | |
| 9,328,288 B2 | 5/2016 | Cohen et al. | |
| 9,534,170 B2 | 1/2017 | Ferrand et al. | |
| 10,094,048 B2 | 10/2018 | Chou | |
| 10,324,198 B2 | 6/2019 | Ferrand | |
| 10,890,670 B2 | 1/2021 | Ferrand | |
| 2002/0144640 A1 | 10/2002 | Andreaco et al. | |
| 2003/0020044 A1 | 1/2003 | Lyons et al. | |
| 2003/0062465 A1 | 4/2003 | Pauwels et al. | |
| 2003/0159643 A1 | 8/2003 | Sumiya et al. | |
| 2004/0108492 A1 | 6/2004 | Derenzo et al. | |
| 2004/0200964 A1 | 10/2004 | Lefaucheur et al. | |
| 2004/0245479 A1 | 12/2004 | Misawa et al. | |
| 2005/0082484 A1 | 4/2005 | Srivastava et al. | |
| 2005/0104000 A1 | 5/2005 | Kindem et al. | |
| 2005/0211906 A1 | 9/2005 | Tonami et al. | |
| 2006/0086311 A1 | 4/2006 | Zagumennyi | |
| 2006/0266277 A1 | 11/2006 | Usui et al. | |
| 2006/0288926 A1 | 12/2006 | Kurata et al. | |
| 2008/0089824 A1 | 4/2008 | Shimura et al. | |
| 2010/0078595 A1 | 4/2010 | Eriksson et al. | |
| 2010/0327227 A1 | 12/2010 | Kurata et al. | |
| 2012/0126171 A1 | 5/2012 | Andreaco et al. | |
| 2014/0061537 A1 | 3/2014 | Zagumennyi | |
| 2014/0291580 A1 | 10/2014 | Zagumennyi | |
| 2015/0069298 A1 | 3/2015 | Kurata et al. | |
| 2016/0002529 A1 | 1/2016 | Blahuta et al. | |
| 2016/0252631 A1 | 9/2016 | Blahuta et al. | |

FOREIGN PATENT DOCUMENTS

| | | |
|---|---|---|
| CN | 1926218 B | 12/2012 |
| CN | 105986320 A | 10/2016 |
| CN | 108186041 A | 6/2018 |
| CN | 210803733 U | 6/2020 |
| DE | 19950087 A1 | 5/2000 |
| EP | 0097296 B1 | 1/1987 |
| EP | 0795631 A1 | 9/1997 |
| EP | 1028154 B1 | 8/2000 |
| EP | 1466955 A2 | 10/2004 |
| JP | 2-300696 | 12/1990 |
| JP | 6-287553 | 10/1994 |
| JP | 2000178554 A | 6/2000 |
| JP | 2001524163 A | 11/2001 |
| JP | 2003253255 A | 9/2003 |
| JP | 2004300418 A | 10/2004 |
| JP | 2004339506 A | 12/2004 |
| JP | 2006083275 A | 3/2006 |
| JP | 2006199727 A | 8/2006 |
| JP | 2006257199 A | 9/2006 |
| JP | 2007001849 A | 1/2007 |
| JP | 2007001850 A | 1/2007 |
| JP | 2007016197 A | 1/2007 |
| JP | 2007514631 A | 6/2007 |
| WO | WO-2005042812 A1 | 5/2005 |
| WO | WO-2015185988 A1 | 12/2015 |

OTHER PUBLICATIONS

Michael E. Fleet et al., "The Structure of NaCa2LuSi2O7F2, a Synthetic Phase of Cuspidine Group", The Canadian Mineralogist, vol. 33, 1995, pp. 879-884.

Office Action dated Oct. 23, 2012, in Japanese Patent Application No. 2007-525327 (with English translation).

Zavartsev, et al, "Czochralski growth and characterisation of large Ce3 + :Lu2Si05 Single crystals co-doped with Mg2 + or Ca2 + or Tb3 + for scintillators", Journal of Growth, vol. 275, No. 1-2, pp. e2167-e2171 (2005}.

Laishun Qin, et al., "Growth and characteristics of LYSO (Lu2(1-x-y)Y2xSiO5:Cey) scintillation crystals," Journal of Crystal Growth, vol. 281 (2005) pp. 518-524.

Letter from Allen, Dyer, Doppelt & Gilchrist, P.A. to Hill, Ward & Henderson, P.A. and Kirkland & Ellis, LLP re *Saint-Gobain Cristaux et Detecteurs* V. *Crystal Photonics, Inc.* Case, dated Sep. 16, 2021, 94 pgs.

DENSE HIGH-SPEED SCINTILLATOR MATERIAL OF LOW AFTERGLOW

CROSS REFERENCE TO RELATED APPLICATIONS

This application is a continuation application of prior U.S. patent application Ser. No. 17/114,824 filed Dec. 8, 2020, which is a continuation of U.S. patent application Ser. No. 16/400,195 filed May 1, 2019, which is a continuation application of prior U.S. patent application Ser. No. 15/358, 341 filed Nov. 22, 2016; now U.S. Pat. No. 10,324,198, which is a continuation application of prior U.S. patent application Ser. No. 14/039,888 filed Sep. 27, 2013; now U.S. Pat. No. 9,534,170, which is a continuation application of prior U.S. patent application Ser. No. 13/214,648 filed Aug. 22, 2011; now U.S. Pat. No. 8,574,458, which is a divisional application of prior U.S. patent application Ser. No. 12/622,881 filed on Nov. 20, 2009; now U.S. Pat. No. 8,034,258, which is a divisional application of prior U.S. patent application Ser. No. 11/573,323 which is a National Stage of PCT/FR05/50658 filed on Aug. 8, 2005; now U.S. Pat. No. 7,651,632, which claims the benefit of priority under 35 U.S.C § 119 from French Patent Application No. 045181.5, filed Aug. 9, 2004, the entire contents of which are incorporated herein by reference.

BACKGROUND OF THE INVENTION

The invention relates to scintillator materials, to a manufacturing process for obtaining them and to the use of said materials, especially in gamma-ray and/or X-ray detectors.

Scintillator materials are widely used in detectors for gamma rays, X-rays, cosmic rays and particles having an energy of the order of 1 keV and also above this value.

A scintillator material is a material that is transparent in the scintillation wavelength range, which responds to incident radiation by emitting a light pulse.

It is possible to manufacture from such materials, which are generally single crystals, detectors in which the light emitted by the crystal that the detector contains is coupled to a light detection means and produces an electrical signal proportional to the number of light pulses received and to their intensity. Such detectors are used in particular in industry to measure thickness and grammage or coating weight, and in the fields of nuclear medicine, physics, chemistry and oil research.

One family of known scintillator crystals that is used is that of cerium-doped lutetium silicates. Cerium-doped $Lu_2SiO_5$ is disclosed in U.S. Pat. No. 4,958,080, and the U.S. Pat. No. 6,624,420 discloses $Ce_{2x}(Lu_{1-y}Y_y)_{2(1-x)}SiO_5$. Finally, U.S. Pat. No. 6,437,336 relates to compositions of the $Lu_{2(1-x)}M_{2x}Si_2O_7$ type, where M is at least partly cerium. These various scintillator compositions all have in common a high stopping power for high-energy radiation and give rise to intense light emission with very rapid light pulses.

A desirable additional property is to reduce the amount of light emitted after the incident radiation stops (i.e. delayed luminescence or afterglow). Physically, this phenomenon, well known to those skilled in the art, is explained by the presence of electron traps in the crystallographic structure of the material. The phenomenon of scintillation relies on the photoelectric effect, which creates an electron-hole pair in the scintillator material. Upon recombination on an active site (a $Ce^{3+}$ site in the aforementioned scintillators), the electron emits photons via a process that generally takes place in much less than one microsecond. The aforementioned scintillators, which are particularly rapid, result in a pulse duration that decreases with a first-order exponential constant of around 40 ns. However, the trapped electrons do not generate light, but their detrapping by thermal excitation (including at room temperature) gives rise to photon emission—the afterglow—, which still remains measurable after times of greater than one second.

This phenomenon may be unacceptable in applications in which it is desired to isolate each pulse, using very short windowing. This is particularly the case with CT (computed tomography) applications (scanners) that are well known in the medical or industrial sectors. When the CT system is coupled to a PET (Positron Emission Tomography) scanner, which is becoming the standard in industry, the poorer resolution of the CT affects the performance of the entire system and therefore the capability of the clinician to interpret the result of the complete PET/CT system. Afterglow is known to be completely unacceptable for these applications.

Compositions of the lutetium silicates type, disclosed in U.S. Pat. No. 4,958,080 (of the LSO:Ce type, using the notation of those skilled in the art) and U.S. Pat. No. 6,624,420 (of the LYSO:Ce type) are known to generate a significant afterglow. In contrast, the compositions disclosed in U.S. Pat. No. 6,437,336 (of the LPS:Ce type) have the advantage of a much weaker afterglow. These results are given for example by L. Pidol, A. Kahn-Harari, B. Viana, B. Ferrand, P. Dorenbos, J. de Haas, C. W. E. van Eijk and E. Virey in "Scintillation properties of $Lu_2Si_2O_7:Ce^{3+}$, a fast and dense scintillator crystal", *Journal of Physics: Condensed Matter*, 2003, 15, 2091-2102. The curve shown in FIG. 1 is extracted from this article and represents the amount of light detected in the form of the number of events (or counts) per mg of scintillator material as a function of time, under X-ray excitation for a few hours. The LPS:Ce composition gives a significantly better result in terms of afterglow.

The behavior of LYSO is very similar to that of LSO from this standpoint. The reduction in this afterglow forms the subject of the present application.

The afterglow property may be demonstrated more fundamentally by thermoluminescence (see S. W. S. McKeever "Thermoluminescence of solids", Cambridge University Press (1985)). This characterization consists in thermally exciting a specimen after irradiation and measuring the light emission. A light peak close to room temperature at 300 K corresponds to an afterglow of greater or lesser magnitude depending on its intensity (detrapping). A peak at a higher temperature corresponds to the existence of traps that are deeper but less susceptible to thermal excitation at room temperature. This is illustrated in FIG. 2, extracted from the aforementioned article by L. Pidol et al., which shows, in another way, the advantage of a composition of the LPS type in terms of afterglow.

However, compositions of the LPS type have the drawback of a lower stopping power than those of the LSO or LYSO type. This situation stems simply from the average atomic number of the compound and from the density of the associated phase.

BRIEF SUMMARY OF THE INVENTION

Thermoluminescence measurements may be carried out using an automated TL-DA-15 instrument, manufactured by RISO (Denmark), shown schematically in FIG. 3. The heater, the thermocouple and a "lift", allowing the specimen to be positioned, are in alignment with the photomultiplier (PM) and with optical filters. Inside the analysis chamber, which is under a stream of nitrogen, a pivoting table (pivoting specimen holder) actuated by a motor is able to position the specimen either in front of the radioactive source (placed in a lead container) for the irradiation step, or between the heater and the photomultiplier for the thermoluminescence measurements. Before each measurement, the crystals, which are about 1 mm in thickness, are heated for a few minutes to 672 K. Next, they are irradiated and then the thermoluminescence curves are recorded under a stream of nitrogen, with a constant heating rate between 313 and 672 K. Measurements at higher temperatures are not possible because of the black body radiation ("black body radiation" is the light spontaneously emitted by a substance that is heated to incandescence). Each curve is normalized with respect to the mass of product.

In our case, the emission that interests us is that from the cerium ion, between about 350 and 450 nm. We have chosen matched filters (HA3 and 7-59) at the entry of the photomultiplier. For quantitative measurements, the irradiation takes place in situ by a $^{90}Sr/^{90}Y$ β-source delivering a dose of 3.6 gray/h in air. The parameters that can be varied during the TL (thermoluminescence) measurements are the dose (irradiation time, here 20 s) and the heating rate (here, 0.5 K/s).

The Applicant has discovered that the addition of a divalent alkaline earth metal M and/or of a trivalent metal M' to an LYSO-type composition very substantially reduces the afterglow. In particular, M may be Ca, Mg or Sr (in divalent cation form). In particular, M' may be Al, Ga or In (in trivalent cation form). The element M substitutes for Y or Lu and the element M' substitutes for Si.

DETAILED DESCRIPTION OF THE INVENTION

Figure 1:
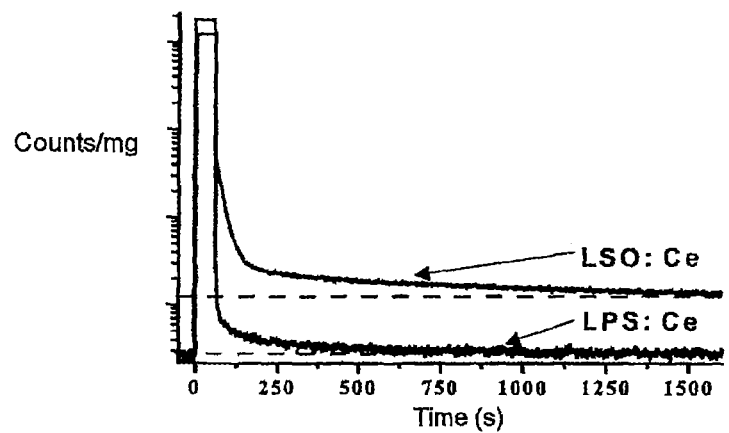
FIG. 1 is a diagram showing the amount of light detected in the form of the number of events (or counts) per mg of scintillator material as a function of time, under X-ray excitation for a few hours.
Figure 2:
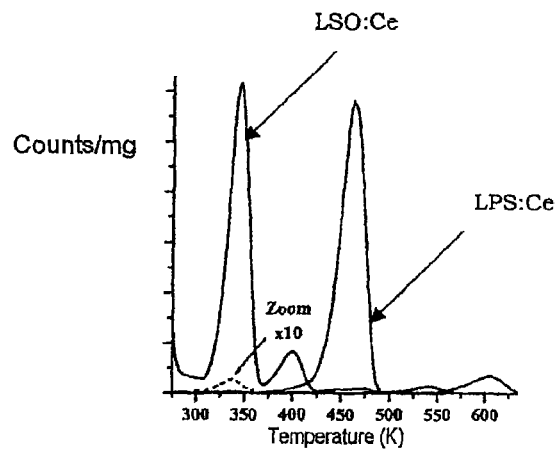
FIG. 2 is a diagram showing the amount of light measured as a function of temperature.
Figure 3:
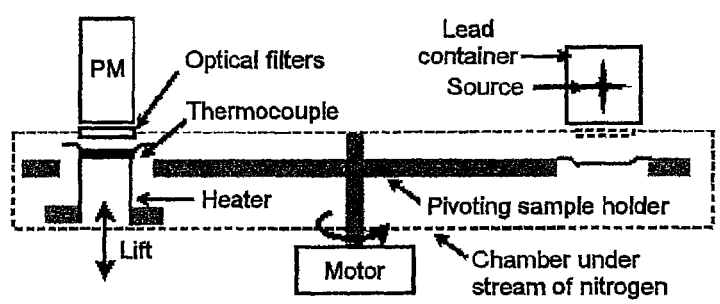
FIG. 3 is a schematic diagram of an automated TL-DA-15 instrument, manufactured by RISO (Denmark).

Surprisingly, the products according to the invention, thanks to the introduction of M, especially Ca, reduce the afterglow without affecting the density within the proportions considered.

The scintillator material according to the invention is of formula:

$$Lu_{(2-y)}Y_{(y-z-x)}Ce_xM_zSi_{(1-v)}M'_vO_5 \quad \text{(Formula 1)}$$

in which:
M represents a divalent alkaline earth metal, such as Ca, Mg or Sr, and M' represents a trivalent metal, such Al, Ga or In, (z+v) being greater than or equal to 0.0001 and less than or equal to 0.2;
z being greater than or equal to 0 and less than or equal to 0.2;
v being greater than or equal to 0 and less than or equal to 0.2;
x being greater than or equal to 0.0001 and less than 0.1; and
y ranging from (x+z) to 1.
Preferably, (z+v) is greater than or equal to 0.0002.
Preferably, (z+v) is less than or equal to 0.05 and more preferably less than or equal to 0.01, and even less than 0.001.
Preferably, x is greater than 0.0001 and less than 0.001.
In particular, v may be zero (absence of M'), in which case z is at least 0.0001.

In particular, the scintillator material according to the invention may be such that v is zero. The scintillator material according to the invention may also be such that M is Ca, which corresponds to a particularly suitable composition. The combination of v being zero with M being Ca as particularly suitable. The composition according to the invention then has the following formula:

$$Lu_{(2-y)}Y_{(y-z-x)}Ce_xCa_zSiO_5 \quad \text{(Formula II)}$$

The scintillator material according to the invention may in particular also be such that z is zero. The scintillator material according to the invention may in particular also be such that M' is Al. The combination of z being zero with M' being Al is particularly suitable. The composition according to the invention then has the following formula:

$$Lu_{(2-y)}Y_{(y-x)}Ce_xAl_vSi_{(1-v)}O_5 \quad \text{(Formula III)}$$

The molar content of the element 0 is substantially five times that of (Si+M'), it being understood that this value may vary by about ±2%.

The scintillator material according to the invention can be obtained in the form of a single crystal or a single crystal by Czochralski growth.

The invention also relates to the use of the scintillator material according to the invention as a component of a radiation detector, in particular a gamma-ray and/or X-ray detector, especially in CT (Computed Tomography) scanners.

The invention also relates to the use of the scintillator material according to the invention as a component of a scintillation detector, especially for applications in industry, for the medical field and/or for detection in oil drilling. In particular, this involves any scintillator system with continuous acquisition (which include CT tomography). Also involved is any scintillator system of the positron emission tomography type, especially with time-of-flight measurement), optionally combined with emission tomography.

Without the Applicant being tied down to any particular theoretical argument, it is assumed that the introduction of a divalent alkaline earth metal ion M substituting for a trivalent rare-earth ion, or of a trivalent metal ion M' substituting for a tetravalent silicon atom, creates a positive charge deficit that limits the trapping of electrons responsible for the afterglow.

EXAMPLES

Three LYSO:Ce single crystals 1 inch in diameter were produced using the Czochralski method under conditions identical to those described in the aforementioned patents. To do this, raw materials corresponding to the following compositions were used:

Control (with no Ca):

$$Lu_{1.8}Y_{0.1978}Ce_{0.0022}SiO_{4.9961}$$

Composition 1: $Lu_{1.8}Y_{0.1778}Ca_{0.02}Ce_{0.0022}SiO_{4.9961}$

Composition 2: $Lu_{1.8}Y_{0.1878}Ca_{0.01}Ce_{0.0022}SiO_{4.9961}$

The charges were prepared from the corresponding oxides (Ca, Ce, Lu, Y oxides) so as to obtain the desired formulae. The actual Ce and Ca concentrations in the final crystal were lower than those introduced via the raw materials through segregation during crystal growth.

The single crystals finally obtained, of formula $Lu_{(2-y)}Y_{(y-z-x)}Ce_xCa_zSiO_5$, had the following compositions at the top of the specimen:

|   | Control (no Ca) | Composition 1 | Composition 2 |
|---|---|---|---|
| x | 0.00026 | 0.00031 | 0.00036 |
| y | 0.095 | 0.095 | 0.095 |
| z | 0 | 0.00041 | 0.00023 |

Composition 1 gave a significantly lower afterglow than the control composition (of the conventional LYSO type) and an estimated light level of 20 000 photons/MeV under excitation by a $^{137}Cs$ gamma-ray source, i.e. slightly less than the LPS composition (26 000 photons/MeV), the LYSO composition (34 000 photons/MeV) and the LSO composition (about 28 000 photons/MeV). Such a light level is far from unacceptable for most applications. Bismuth germanate ($Bi_4Ge_3O_{12}$), very widely used, emits only 9 000 photons/MeV. Overall, composition 1 has as much stopping power as an LYSO-type composition without significantly losing out in terms of light level, while still significantly reducing the afterglow.

Composition 2 is even more advantageous, with a still lower afterglow and a light yield of 27 000 photons/MeV.

Figure 4:
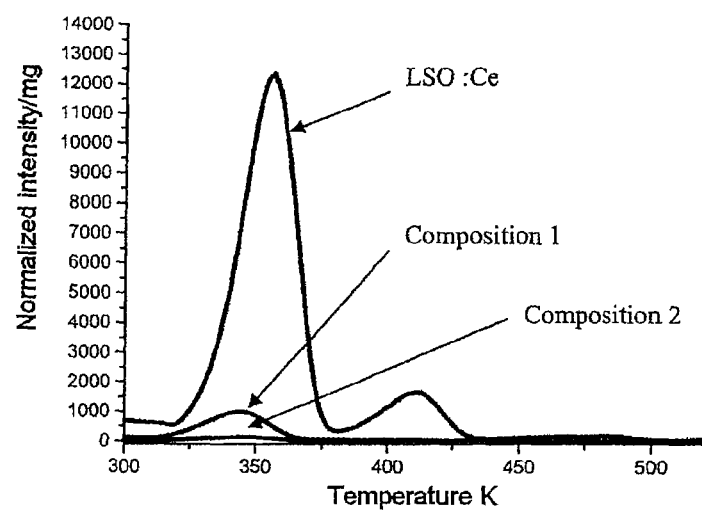
FIG. 4 is a diagram comparing the afterglow values of compositions 1 and 2 with a conventional LSO.

FIG. 4 compares the afterglow values of compositions 1 and 2 with a conventional LSO (the control).

The invention claimed is:

1. An inorganic LYSO-type scintillator material comprising Lu, Y, Si, O, Ce, M, and optionally M' wherein:
the relative amounts of Lu, Y, Si, O, Ce, M, and M' satisfy formula (1):

$$Lu_{(2-y)}Y_{(y-z-x)}Ce_xM_zSi_{(1-v)}M'_vO_5 \quad (1);$$

M represents a divalent alkaline earth metal and M' represents a trivalent metal;
(z+v) is greater than or equal to 0.0001 and less than or equal to 0.2;
z is greater than 0 and less than or equal to 0.2;
v is greater than or equal to 0 and less than or equal to 0.2;
x is greater than or equal to 0.0001 and less than 0.1; and
y is from (x+z) to 1.

2. The inorganic scintillator material according to claim 1, wherein (z+v) is greater than or equal to 0.0002.

3. The inorganic scintillator material according to claim 1, wherein (z+v) is less than or equal to 0.05.

4. The inorganic scintillator material according to claim 1, wherein (z+v) is less than or equal to 0.01.

5. The inorganic scintillator material according to claim 1, wherein (z+v) is less than 0.001.

6. The inorganic scintillator material according to claim 1, wherein x is greater than 0.0001 and less than 0.001.

7. The inorganic scintillator material according to claim 1, wherein z is at least 0.0001.

8. An inorganic LYSO-type scintillator material comprising Lu, Y, Si, O, Ce, M, and optionally M' wherein:
the relative amounts of Lu, Si, O, Y, Ce, and M or M' satisfy formula (1):

$$Lu_{(2-y)}Y_{(y-z-x)}Ce_xM_zSi_{(1-v)}M'_vO_5 \quad (1);$$

M represents a divalent alkaline earth metal and M' represents a trivalent metal;
(z+v) is greater than or equal to 0.0001 and less than or equal to 0.2;
z is greater than 0 and less than or equal to 0.2;
v is greater than or equal to 0 and less than or equal to 0.2;
x is greater than or equal to 0.0001 and less than 0.1;
y is from (x+z) to 1; and
the inorganic scintillator material is a single crystal.

9. The inorganic scintillator material according to claim 8, wherein (z+v) is greater than or equal to 0.0002.

10. The inorganic scintillator material according to claim 8, wherein (z+v) is less than or equal to 0.05.

11. The inorganic scintillator material according to claim 8, wherein (z+v) is less than or equal to 0.01.

12. The inorganic scintillator material according to claim 8, wherein (z+v) is less than 0.001.

13. The inorganic scintillator material according to claim 8, wherein x is greater than 0.0001 and less than 0.001.

14. The inorganic scintillator material according to claim 8, wherein z is at least 0.0001.

15. A radiation detector comprising an inorganic LYSO-type scintillator material comprising Lu, Y, Si, O, Ce, M, and optionally M' wherein:
the relative amounts of Lu, Si, O, Y, Ce, and M or M' satisfy formula (1):

$$Lu_{(2-y)}Y_{(y-z-x)}Ce_xM_zSi_{(1-v)}M'_vO_5 \quad (1);$$

M represents a divalent alkaline earth metal and M' represents a trivalent metal;
(z+v) is greater than or equal to 0.0001 and less than or equal to 0.2;
z is greater than 0 and less than or equal to 0.2;
v is greater than or equal to 0 and less than or equal to 0.2;
x is greater than or equal to 0.0001 and less than 0.1; and
y is from (x+z) to 1.

16. The radiation detector according to claim 15, wherein an inorganic scintillator material is a single crystal.

17. The radiation detector according to claim 15, wherein the radiation detector is a positron emission tomography detector.

18. The radiation detector according to claim 15, wherein the radiation detector is a time-of-flight positron emission tomography detector.

19. The radiation detector according to claim 15, wherein the inorganic scintillator material is coupled to a light detector which produces an electrical signal proportional to a number of light pulses received by the light detector and the intensity of the light pulses received by the light detector.

* * * * *